(12) United States Patent
Barr (10) Patent No.: US 8,808,223 B2
(45) Date of Patent: Aug. 19, 2014

(54) DEVICE FOR CONTROLLING THE RATE OF FLOW OF A FLUID

(75) Inventor: Richard Henry Howard Barr, Devon (GB)

(73) Assignee: Centrax Limited, Newton Abbot, Devon (GB)

(*) Notice: Subject to any disclaimer, the term of this patent is extended or adjusted under 35 U.S.C. 154(b) by 828 days.

(21) Appl. No.: 12/600,046

(22) PCT Filed: May 12, 2008

(86) PCT No.: PCT/GB2008/001648
§ 371 (c)(1),
(2), (4) Date: Nov. 13, 2009

(87) PCT Pub. No.: WO2008/142371
PCT Pub. Date: Nov. 27, 2008

(65) Prior Publication Data
US 2010/0305493 A1    Dec. 2, 2010

(30) Foreign Application Priority Data

May 17, 2007    (GB) .................................. 0709537.5

(51) Int. Cl.
*A61M 5/00*    (2006.01)
*A61M 5/168*    (2006.01)
*A61M 27/00*    (2006.01)
(52) U.S. Cl.
CPC ..... *A61M 27/006* (2013.01); *A61M 2205/6054* (2013.01); *A61M 2205/3515* (2013.01); *A61M 5/16881* (2013.01); *A61M 2205/8287* (2013.01)
USPC .............................................. 604/9

(58) Field of Classification Search
USPC ........ 604/8–10, 246–248; 251/118, 126, 127, 251/205, 208; 138/42–45
See application file for complete search history.

(56) References Cited

U.S. PATENT DOCUMENTS 4,537,680 A    8/1985    Barth
4,917,687 A *  4/1990    O'Boyle ....................... 604/248
(Continued)

FOREIGN PATENT DOCUMENTS

DE    19548537 A1    7/1996
DE    19825912 C1    5/1999

OTHER PUBLICATIONS

PCT Preliminary Search Report dated Nov. 17, 2009.
UK Search Report dated Aug. 22, 2007.

(Continued)

*Primary Examiner* — Philip R Wiest
(74) *Attorney, Agent, or Firm* — MacMillan, Sobanski & Todd, LLC (57) ABSTRACT

A device (1) for controlling the rate of flow of a fluid such as fluid which is diverted from a part of a human or animal body. The device comprises: an inlet (2); an outlet (4); and a resistance member (6), operatively connected to the inlet (2) and the outlet (4), the resistance member (6) comprising: a first plate (8), a surface of which comprises a groove which defines a resistance flow channel, an entry of the flow channel being in fluid communication with the inlet (2) and an exit of the flow channel being in fluid communication with the outlet (4); and a second plate (12), the second plate being held in abutment with the grooved surface of the first plate (8) so as to define a resistance (tube 14).

20 Claims, 3 Drawing Sheets

(56) References Cited

U.S. PATENT DOCUMENTS

| | | | |
|---|---|---|---|
| 5,009,251 A | 4/1991 | Pike et al. | |
| 5,637,083 A | 6/1997 | Bertrand et al. | |
| 6,126,628 A | 10/2000 | Nissels | |
| 7,195,608 B2* | 3/2007 | Burnett | 604/9 |
| 7,334,594 B2* | 2/2008 | Ludin | 137/1 |
| 7,842,004 B2* | 11/2010 | Kassem | 604/9 |
| 2002/0022793 A1 | 2/2002 | Bertrand et al. | |
| 2004/0116905 A1 | 6/2004 | Pedersen et al. | |
| 2005/0085763 A1 | 4/2005 | Ginggen et al. | |
| 2007/0005000 A1 | 1/2007 | Ludin | |
| 2007/0093741 A1* | 4/2007 | Miethke | 604/9 |
| 2007/0112291 A1 | 5/2007 | Borgesen | |

OTHER PUBLICATIONS

PCT Search Report dated Jul. 31, 2008.

* cited by examiner

DEVICE FOR CONTROLLING THE RATE OF FLOW OF A FLUID

CROSS REFERENCE TO RELATED APPLICATION

This application is the National Phase of International Application PCT/GB2008/001648 filed May 28, 2008 which designated the U.S. That International Application was published in English under PCT Article 21(2) on Nov. 27, 2008 as International Publication Number WO 2008/142371 A1. PCT/GB2008/001648 claims priority to U.K. Application No. 0709537.5, filed May 17, 2007. Thus, the subject non-provisional application also claims priority to U.K. Application No. 0709537.5, filed May 17, 2007. The disclosures of both applications are incorporated herein by reference.

The present invention relates to a device for controlling the rate of flow of a fluid and may for example, be used to divert fluid from the ventricles of the brain to another part of the body.

BACKGROUND

Hydrocephalus is a defective condition of the brain caused by an imbalance between production of cerebral spinal fluid (CSF) within the brain and the capacity of the brain to re-absorb such fluid at normal pressure. Hydrocephalus may be congenital, accidental or age related and can result in loss of a wide range of physical and mental faculties. The accepted method of treatment of the condition is to divert excess fluid which the brain, through its impairment, is unable to absorb, to some other part of the body such as the right atrium or the peritoneal cavity, where the fluid can re-enter the blood stream. The primary technical challenge associated with this method of treatment is developing the capacity to control the conditions of pressure and flow within the brain in such a manner as to enable lost faculties to be restored, depending on the severity of the condition. This challenge is exacerbated by the greatly differing range of impairment between different patients.

Various devices have been developed to control the pressure and flow conditions within the brain to desired levels. Such devices are commonly known as valves. If the flow imbalance referred to above is not addressed, pressure within the brain rises to an abnormal level. Such increased pressure causes the ventricles of the brain to expand and causes abnormal stress and damage within the brain tissue. Consequently, many valve devices focus on a technology that controls the pressure within the ventricles of the brain directly, restricting that pressure to a desired level and allowing flow rates to vary to accommodate the target pressure. Such devices are referred to as pressure control valves and commonly comprise an orifice that may be forced open by fluid pressure within the brain against some form of resistant mechanism such as a ball and spring or a slit in a tubular member. The majority of valves in use at the present time are pressure control valves. Difficulties with this type of valve arise in being able to set the spring pressure accurately. In addition, the valves are susceptible to malfunction when subject to pressure waves which occur in the brain and they are also very sensitive to changes in pressure due to body posture.

An alternative type of valve directly controls the amount of fluid diverted. Control is effected in such a manner that the desired pressure conditions within the brain are achieved as a secondary effect. Such devices are referred to as flow control valves. Currently available valves control flow by some form of restrictive orifice, which in some cases can be varied to give different flow rates. However, at the pressures existing in the brain (around 12 cm $H_2O$ in a normal supine person), and at the very low diverted flow rates involved (some fraction of 0.35 ml/min) the size of orifice is minute, and it is difficult to predetermine accurately the resulting flow.

SUMMARY OF INVENTION

According to the present invention, there is provided a device for diverting fluid from a part of a human or animal body such as the ventricles of the brain, the device comprising: an inlet; an outlet; and a resistance member, operatively connected to the inlet and the outlet, the resistance member comprising: a first plate, a surface of which comprises a groove which defines a resistance flow channel, an entry of the flow channel being in fluid communication with the inlet and an exit of the flow channel being in fluid communication with the outlet; and a second plate, the second plate being held in abutment with the grooved surface of the first plate so as to define a resistance tube.

The device may divert the fluid to another part of the human or animal body.

A resistance tube such as that provided by the present invention limits flow through the tube by frictional resistance on the walls of the tube. The device of the present invention provides highly predictable and stable control of pressure and flow within the brain of a patient. Due to the nature of the device, it is not substantially influenced by pressure waves within the fluid it diverts and it is far less sensitive to body posture than a pressure control valve.

The device may be configured to be implanted under the skin of, for example, the scalp or chest of a person. It is an advantage of the device that it may be constructed in a highly compact fashion, accommodating the required length of resistance tube within a relatively small surface area. The device can therefore be made sufficiently small and compact to be implanted under the skin of a patient.

The effective hydraulic mean diameter is defined as four times the cross sectional area of the flow in the channel divided by the wetted perimeter of said channel (for example, the hydraulic mean diameter of a circular cross section is the diameter). The effective hydraulic mean diameter of the resistance tube may be between 0.3 mm and 0.8 mm. Optionally, the effective hydraulic mean diameter of the resistance tube is between 0.4 mm and 0.5 mm. For example, the effective hydraulic mean diameter of the resistance tube may be 0.45 mm. The suggested ranges of effective hydraulic mean diameters ensure a desired flow rate is maintained within a device that is of a size suitable for implantation under the skin.

The resistance tube may define a convoluted fluid flow path. For example, it may be folded back on itself at least once. Such a convoluted flow path enables the device to accommodate the high length to diameter ratio required for functionality whilst remaining compact and occupying a relatively small surface area.

The exit of the resistance tube may communicate with the outlet via a selection means. The selection means imparts an element of selectivity and flexibility to the device.

The resistance tube may comprise at least two exits along its length, each of which may be placed in fluid communication with the outlet by the selection means so as to vary the effective length of the resistance tube. By varying the effective length of the resistance tube, it is possible to tailor the device to treat patients having greatly differing levels of impairment.

The exit may comprise an orifice in one of the first and second plates, which orifice may be covered or uncovered by the selection means.

The selection means may comprise a rotor mounted adjacent the resistance member and having a through passage, the rotor being mounted in the device for rotation relative to the resistance member, such that an exit of the resistance tube may be brought into fluid communication with the outlet via the through passage.

The selection means may be magnetically excitable, such that it may be operated via a magnet held proximate the device. The device may therefore be operated transcutaneously. Once implanted, the device may be adjusted to suit the changing needs of a patient in situ, without the need for further surgical intervention.

The resistance tube may define a fluid flow path comprising a plurality of sectors, each sector having an associated exit that may be selected by the selection means.

The selection means may be a sliding fit with the resistance member. Alternatively or in addition, the device may comprise a biasing means, which resiliently urges the selection means into engagement with the resistance member.

The biasing means may comprise a spring, a leaf spring or a helical spring, a Belleville washer or a resilient element.

The device may further comprise a biased ratchet or brake that releasably retains the selection means in a selected rotational orientation. The selection means is thus securely held in its desired position when not being adjusted.

The selection means may further comprise a magnetic marker, which may be provided in the selection means, such that the orientation of the selection means may be determined through use of a compass or magnetic indicator held proximate the device. Such a marker assists in monitoring the operation of the device and in adjusting the device if necessary.

The device may further comprise a filter at the inlet of the device. The filter reduces the possibility of the resistance tube becoming occluded.

The device may further comprise an anti reflux mechanism at the outlet of the device. Such a mechanism ensures that reflux back towards the origin of the fluid cannot take place for any reason.

The groove on the first plate may be formed in any appropriate manner. For example, the grove may be milled, laser cut, electro-discharge machined, electro-chemically machined, chemically etched, or moulded. Such techniques enable the resistance channel, and hence the resistance tube, to be machined to the extremely high tolerances required to achieve accuracy of flow control.

The device may be formed from a biocompatible material selected from titanium, stainless steel alloy, or composite material.

The device may further comprise a fixing element that maintains the first and second plates in abutment. For example, the fixing element may comprise one of a screw, a weld, a glue joint, a brazed joint or a cap.

The inlet and the outlet may each define an axis and the axes of the inlet and outlet may not be parallel. Such positioning of the inlet and outlet facilitates routing of tubing to the area of the body where fluid is to be discharged.

The device may further comprise at least one additional plate, held in abutment with one of the first and second plates.

A surface of the first plate opposite the grooved surface may also comprise a groove which defines a resistance flow channel, and the additional plate may be held in abutment with this second grooved surface of the first plate so as to define a further resistance tube.

The additional plate may be held in abutment with the second plate, a surface of the additional plate may comprise a groove which defines a resistance flow channel, such that the groove on the additional plate, in combination with the second plate that is held in abutment with the grooved surface of the additional plate, defines a further resistance tube. The further resistance tube provides additional resistance length and adds flexibility to the device without causing the device to increase in size significantly.

The further resistance tube may be in fluid communication with the first resistance tube. The resistance tube and further resistance tube are thus connected in series to form a compound resistance tube of greater length and hence greater resistance to flow.

The further resistance tube may be in fluid communication with the inlet, such that the resistance tube is in fluid communication with the inlet via the further resistance tube.

In a preferred embodiment, the device diverts fluid from the ventricles of the human or animal brain to another part of the human or animal body, such as the peritoneal cavity or right atrium.

The first, second or additional plates may be provided with a rim about an outer edge, such that the rim may be arranged to contain the one or more other plates. For example, the rim may be formed on one side of the first, second or additional plates, such that the remaining plates may fit inside the rim. Alternatively, the rim may extend on both sides of the first plate, such that the second and additional plates may fit inside the rim on either side of the first plate. The rim may also extend on both sides of the second plate, such that the first and additional plates may fit inside the rim on either side of the second plate. The first, second or additional plates may therefore form a module separate from the main casing, which may be flow pressure tested independently prior to assembly in the main casing.

Surfaces of the resistance member may be provided with an antibiotic coating. In particular, surfaces of the first, second and/or additional plates may be provided with an antibiotic coating, such that the surfaces of the resistance tube and/or further resistance tube are coated with said antibiotic coating, thereby preventing the growth of any undesirable bacterial deposits. The inlet, outlet, anti-reflux mechanism and/or filter may also be coated with an antibiotic coating.

According to another aspect of the present invention, there is provided a method of treating hydrocephalus by diverting fluid from the ventricles of the brain to another area of the body via a resistance tube, the resistance tube being formed by a grooved surface of a first plate that is held in abutment with a planar surface of a second plate.

According to another aspect of the present invention, there is provided a flow control device comprising: an inlet; an outlet; and a resistance member, operatively connected to the inlet and the outlet, the resistance member comprising: a first plate, a surface of which comprises a groove which defines a resistance flow channel, an entry of the flow channel being in fluid communication with the inlet and an exit of the flow channel being in fluid communication with the outlet; and a second plate, the second plate being held in abutment with the grooved surface of the first plate so as to define a resistance tube, wherein the exit of the resistance tube communicates with the outlet via a selection means, and wherein the resistance tube comprises at least two exits along its length, each of which may be placed in fluid communication with the outlet by the selection means so as to vary the effective length of the resistance tube.

BRIEF DESCRIPTION OF THE DRAWINGS

For a better understanding of the present invention, and to show more clearly how it may be carried into effect, reference will now be made, by way of example, to the accompanying drawings, in which:—

DETAILED DESCRIPTION OF PREFERRED EMBODIMENTS

Figure 1:
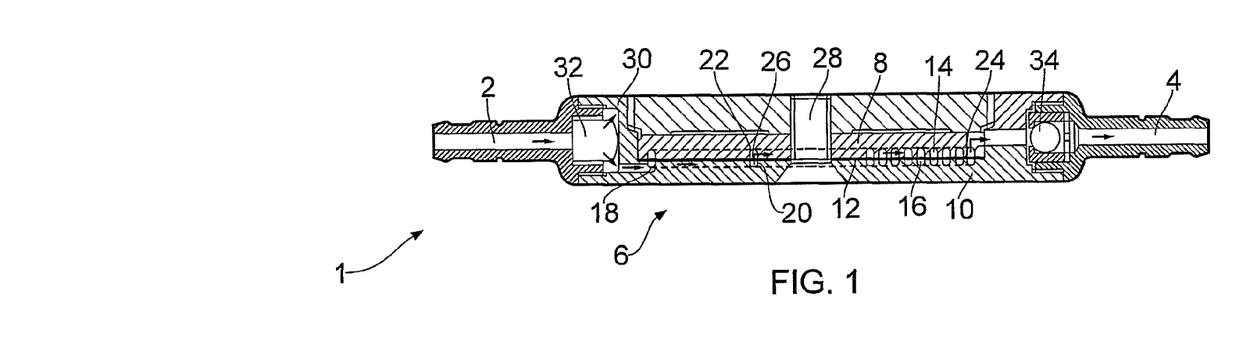
FIG. 1 is a sectional view of a device for diverting fluid.
Figure 2:
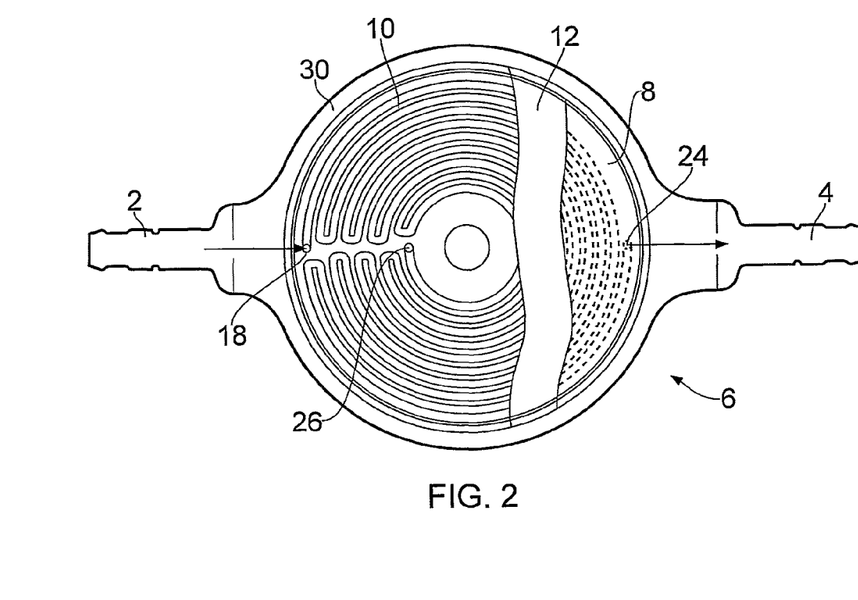
FIG. 2 is a partially cut away sectional view of the device of FIG. 1, taken at 90 degrees to the view of FIG. 1.

With reference to FIGS. 1 and 2, a device 1 for diverting fluid from the ventricles of the brain comprises an inlet 2, an outlet 4 and a resistance member 6 operatively coupled between the inlet 2 and the outlet 4. The resistance member 6 comprises an upper member 8, a lower member 10 and a substantially circular plate 12 sandwiched between the upper and lower members 8, 10. The upper and lower members 8, 10 each have a substantially circular, planar surface in contact with the plate 12. The planar surfaces of the upper and lower members 8, 10 each comprise a groove or channel, which forms a continuous closed resistance tube 14, 16 when the grooved surface is in abutment with the plate 12. The lower resistance tube 16 formed by the lower member 10 follows a convoluted flow path from a fluid entry point 18, at a radially outer position on the planar surface of the lower member 10, to a fluid exit point 20, at a radially inner position on the planar surface of the lower member 10. The fluid entry point 18 of the lower resistance tube 16 is in fluid communication with the inlet 2 of the device 1. The upper resistance tube 14 formed by the upper member 8 follows a convoluted flow path from a fluid entry point 22, at a radially inner position on the planar surface of the upper member 8, to a fluid exit point 24, at a radially outer position on the planar surface of the upper member 8. The fluid exit point 24 of the upper resistance tube 14 is in fluid communication with the outlet 4 of the device 1. The fluid exit point 20 on the lower resistance tube 16 corresponds to and is aligned with the fluid entry point 22 on the upper resistance tube 14. The exit/entry point 20/22 comprises an orifice 26 in the plate 12, permitting fluid communication between the two resistance tubes 14, 16 such that the two resistance tubes 14, 16 form a compound resistance tube having two superimposed layers. The illustrated convoluted flow paths of the resistance tubes 14, 16 comprise a series of arcs, each flow path folding back upon itself at the tip of each arc and thus meandering from a radially outer position to a radially inner position or vice versa. Convoluted flow paths between the entry and exit point of the resistance tubes 14, 16 having different shapes and/or orientations are also contemplated.

The device 1 may comprise additional members (not shown) within the resistance member 6, each having a grooved surface in abutment with a planar surface in order to form a further length of resistance tube. In this manner a compound resistance tube of many layers may be provided without increasing the surface area occupied by the device 1.

The plate 12 and upper and lower members 8, 10 of the resistance member 6 are maintained in abutment with one another by a single central screw 28. Alternatively, the components of the resistance member may be held together by laser welding, brazing, gluing or any other appropriate means of fixation. The lower member 10 of the resistance member 6 is integrally formed with the inlet 2 and the outlet 4. A rim 30 extends around the circumference of the resistance member 6 and, together with the integral structure of the lower member 10, the inlet 2 and the outlet 4, forms a casing of the device 1 within which the remaining components are mounted.

A filter 32 is mounted in the inlet 2 of the device 1, in the fluid flow path from the inlet 2 to the entry 18 to the lower resistance tube 16. An anti-reflux mechanism 34 is mounted in the outlet 4 of the device 1, in the fluid flow path from the exit 24 of the upper resistance tube 14 to the outlet 4. The anti-reflux mechanism may be a non-return ball valve and may be spring-loaded. Alternatively, the mechanism 34 may be any other suitable anti-reflux mechanism.

In the illustrated embodiment, the axes of the inlet 2 and outlet 4 are parallel. However, to facilitate routing of tubing leading from the outlet 4 to the area of the body selected for discharge of the fluid, it may be desirable for the axes of the inlet 2 and outlet 4 be angled with respect to one another.

In an advantageous application, the device 1 is mounted under the skin of a patient, but for tests or other purposes the device may be mounted externally, such as on the skin or even remote from the body, for example on clothing. CSF fluid from the brain enters the device 1 via the inlet 2 and passes through the filter 32. The filter 32 prevents occlusion of the resistance tubes 14, 16 by filtering from the CSF any particles of debris that might block the resistance tubes. Such debris may be particularly prevalent immediately after surgery. From the filter 32, CSF flows through the entry point 18 and into the lower resistance tube 16. CSF flows through the lower resistance tube 16 to the exit point 20. At exit point 20, CSF passes through the orifice 26 in the plate 12 and through the entry point 22 into the upper resistance tube 14. CSF then flows through the upper resistance tube 14 to the exit point 24. From the exit point 24, CSF flows through the anti-reflux mechanism 34 and passes out of the device 1 via the outlet 4. The anti-reflux mechanism prevents any reflux of CSF back towards the brain as a result of pressure changes caused by changes in body posture or for any other reason. The outlet 4 may be connected to appropriate tubing (not shown) to convey the CSF from the device 1 to the desired discharge area.

Frictional resistance from the walls of the resistance tubes 14, 16 limits CSF flow through the device to the desired flow rate. In order to achieve consistency of flow for a given length of resistance tube and pressure drop over the tube, the grooves on the upper and lower members 8, 10 that form the resistance tubes 14, 16 must be made to very close tolerances. From Poiseuille's equation, flow rate varies as the fourth power of channel diameter for a given length, pressure drop and fluid viscosity. Consequently, a small channel of approximately 0.5 mm effective diameter must be made to extremely close tolerances if the desired level of flow control is to be achieved. A preferred method of producing the grooves that form the resistance tubes, enabling the production of various contours over the length of the grooves, is CNC milling using a small end mill. This method of production is flexible, enabling the production of varying shapes and cross sections as desired. Other possible methods for forming the grooves include laser cutting, electro-discharge or electro-chemical machining, chemical etching or moulding from a die if a suitable material is chosen. Suitable biocompatible materials for the device include titanium or stainless steel. Alternatively, a biocompatible composite would be required for moulding, for example High Density Polyethylene (HDPE), Ultra High Molecular Weight Polyethylene (UHMWPE) or Polyetheretherketone (PEEK).

The device described above and illustrated in FIGS. 1 and 2 has fixed characteristics of pressure and flow in accordance with the length and effective diameter of the upper and lower resistance tubes 14, 16. In normal cases of hydrocephalus, such fixed characteristics are acceptable. However, in certain more complicated cases, it may not be possible to predict with accuracy the flow conditions required to compensate for the impairment of the brain. Consequently, it is desirable to be able to vary the pressure and flow characteristics of the device post operatively in a non-invasive manner. The characteristics of the device could then be adapted according to postoperative observations of a patient. This can be achieved using the device 101 of FIGS. 3, 4a and 4b.

Figure 3:
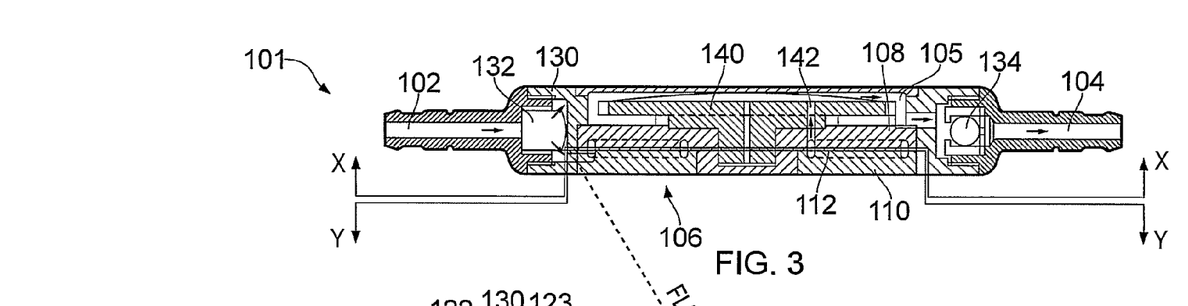
FIG. 3 is a sectional view of an alternative embodiment of device for diverting fluid.
Figure 4A:
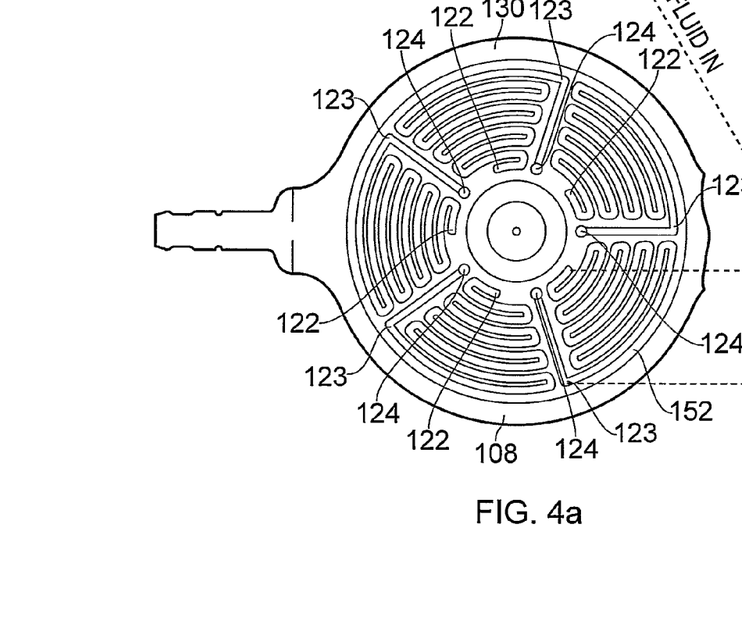
FIG. 4a is a sectional view of the device of FIG. 3, taken along the line XX of FIG. 3.
Figure 4B:
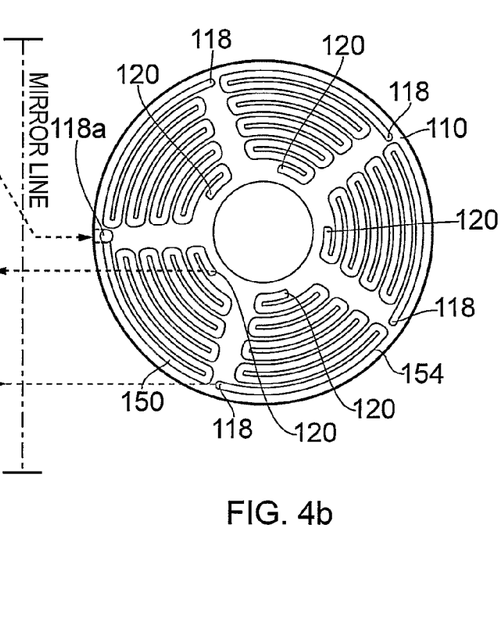
FIG. 4b is a sectional view of the device of FIG. 3, taken along the line YY of FIG. 3.

With reference to FIGS. 3, 4a and 4b, the alternative device 101 for diverting fluid from the ventricles of the brain comprises an inlet 102, an outlet 104 and a resistance member 106 operatively coupled between the inlet 102 and the outlet 104. The resistance member 106 comprises an upper member 108, a lower member 110 and a substantially circular plate 112 sandwiched between the upper and lower members 108, 110. The lower member 110 is integrally formed with the inlet 102 and the outlet 104. A rim 130 extends around the circumference of the resistance member 106 and, together with the integral structure of the lower member 110, the inlet 102 and the outlet 104, forms a casing of the device 101 within which the remaining components are mounted.

The upper and lower members 108, 110 each have a substantially circular, planar surface in contact with the plate 112. The planar surfaces of the upper and lower members 108, 110 each comprise a plurality of grooves or channels, each of which forms a continuous, closed resistance tube when the grooved surfaces are in abutment with the plate 112. Each groove on the planar surface of the upper member 108 forms an upper resistance tube that follows a convoluted flow path occupying a single sector of the plane circular area of the adjacent surface of the plate 112. Similarly, each groove on the planar surface of the lower member 110 forms a lower resistance tube that follows a convoluted flow path occupying a corresponding sector of the plane circular area of the opposite surface of the plate 112.

With reference to FIG. 4b, each lower resistance tube defined by the lower member 110 follows a convoluted flow path from an entry point 118 at a radially outer position on the member 110, to an exit point 120 at a radially inner position on the member 110. An entry point 118a of one of the lower resistance tubes is in fluid communication with the inlet 102 of the device 101. With reference to FIG. 4a, each upper resistance tube defined by the upper member 108 follows a convoluted flow path from an entry point 122 at a radially inner position on the member 108 to a connection point 123 at a radially outer position on the member 108. From the connection point 123, each upper resistance tube defined by the upper member 108 then follows a direct flow path to an exit point 124 at a radially inner position on the upper member 108. The exit point 120 of each lower resistance tube corresponds to the entry point 122 of a corresponding upper resistance tube. Each pair of corresponding entry and exit points is in fluid communication via an orifice in the plate 112 that is sandwiched between the upper and lower members 108, 110. Similarly, the entry point 118 of each lower resistance tube corresponds to the connection point 123 of a different corresponding upper resistance tube. Each pair of corresponding entry and connection points is in fluid communication via an orifice in the plate 112. In this manner, a compound resistance tube of two layers is formed in which the fluid flow path occupies first the lower and then the upper resistance tube of each sector of the device 101 sequentially.

The device 101 may comprise additional members (not shown) within the resistance member 106, each having a grooved surface in abutment with a planar surface in order to form a resistance tube. In this manner a compound resistance tube of many layers may be provided without increasing the surface area occupied by the device 101.

The illustrated convoluted flow paths of the upper and lower resistance tubes comprise a series of sector arcs, each flow path folding back upon itself at the tip of each arc and thus meandering from a radially outer position of the sector to a radially inner position of the sector or vice versa. Convoluted flow paths between the entry and exit points of the lower resistance tubes and entry and connection points of the upper resistance tubes having a different shape or orientation are also contemplated.

The exit point 124 of each upper resistance tube may be placed in fluid communication with the outlet 104 of the device 101 via a selection rotor 140. The selection rotor 140 is mounted for rotation about the centre point of the resistance tube sectors and comprises a planar face that is held in abutment with, and may be spring loaded against, the surface of the upper member 108 that is opposite to the grooved surface. The rotor 140 comprises a single through passage 142, which passage is in fluid communication with the outlet 104 via the chamber 105 within which the rotor 140 is mounted. The opening of the passage 142 on the planar face of the rotor 140 is at the same radial position as the exit points 124 of the upper resistance tubes. The opening of the through passage 142 may therefore be brought into alignment with the exit point 124 of any one of the upper resistance tubes merely by moving the rotor 140 to the appropriate rotational position. The exit points 124 of the remaining upper resistance tubes are sealed off by the planar face of the rotor 140. The compound resistance tube formed by the upper and lower resistance tubes thus has a fixed entry point 118a, that is in fluid communication with the inlet 102 of the device 101, and a series of possible exit points 124, each of which may be placed in fluid communication with the outlet 104 of the device 101. The effective length of the compound resistance tube, and hence the pressure and flow characteristics of the device 101, may therefore be varied by bringing different exit points 124 into fluid communication with the outlet 104.

The rotor 140 is magnetically excitable, so that it may be moved to a different rotational position through the correct orientation of a magnet brought into close proximity to the rotor 140. In addition, the position of the rotor 140 may be determined even when the rotor is obscured from view (for example when the device is implanted under the skin) by holding a compass adjacent the rotor. The rotational position of the rotor may be stabilised by a spring-loaded ratchet (not shown) operating between the rotor and the surrounding casing such that a substantial torsional magnetic force must be exerted on the rotor 140 to move it from a particular rotational position. Alternatively, it may be located simply by frictional forces caused by the spring loading.

A filter 132 is mounted in the inlet 102 of the device 101, in the fluid path from the inlet 102 to the entry point 118a of the lower resistance tube that is connected to the inlet 102. An anti-reflux mechanism 134 is mounted in the outlet 104 of the device 101, in the fluid path from the through passage 142 of the rotor 140 to the outlet 104. The mechanism may be a non return ball valve and may have a light spring loading. Alternatively, the mechanism 134 may be any other suitable anti-reflux mechanism.

In the illustrated embodiment, the axes of the inlet 102 and outlet 104 are parallel. However, to facilitate shaping of tubing leading from the outlet 104 to the area of the body selected for discharge of the fluid, it may be desirable for the axes of the inlet 102 and outlet 104 be angled with respect to one another.

In an advantageous application, the device 101 is mounted under the skin of a patient. CSF fluid from the brain enters the device 101 via the inlet 102 and passes through the filter 132. The filter 132 prevents occlusion of the resistance tubes by filtering from the CSF any particles of debris that might block the resistance tubes. From the filter 132, CSF flows through the first entry point 118a and into the first sector of the compound resistance tube. CSF initially enters the first lower resistance tube 150. CSF flows through the first lower resistance tube 150 to the exit point 120 of the first lower resistance tube 150. CSF then flows through the adjacent orifice in the plate 112 and into the first upper resistance tube 152 via the associated entry point 122. CSF then flows through the first upper resistance tube 152 to the connection point 123 of the first upper resistance tube 152. If the rotor 140 has placed the exit point 124 of the first upper resistance tube in fluid communication with the outlet 104, then the CSF flows from the connection point 123 to the exit point 124 and via the through passage 142 to the anti-reflux mechanism 132 and out of the device 101 via the outlet 104. If, however, the rotor 140 has sealed off the exit point 124 of the first upper resistance tube 152, then the CSF flows from the connection point 123 through the adjacent orifice in the plate 112 and into the second sector of the compound resistance tube. CSF initially enters the second lower resistance tube 154 via the entry point 118 of the second lower resistance tube 154. CSF then flows sequentially through the sectors of the compound resistance tube (entering each new sector via the lower resistance tube and exiting each sector via the upper resistance tube) until the sector of compound resistance tube that is in fluid communication with the outlet is reached.

Before implantation, the effective length of compound resistance tube required for a particular patient is estimated and the rotor 140 is moved to place the appropriate exit point 124 in fluid communication with the outlet 104. If, after implantation of the device 101, it is determined that the length of compound resistance tube needs to be adjusted, in order to provide different pressure/flow characteristics, a compass is placed adjacent the skin covering the device 101 in order to determine the rotational orientation of the rotor 140. A magnet is then brought into close proximity with the device and used to move the rotor 140 to the desired new rotational position.

In a variation of the embodiment of FIGS. 3 and 4, the components of the device, specifically the upper and lower members of the resistance member 106 and the rotor 140, may be arranged as a sliding fit, so that biasing means is not required.

In the embodiments described above and illustrated in FIGS. 1 to 4b, the upper and lower resistance tubes, or sectors of resistance tube, are formed by grooved surfaces of the upper and lower members 8, 10, 108, 110 of the resistance member 6, 106 being held in abutment with planar surfaces of a central plate 12, 112. In alternative embodiments, the groves that define the resistance tubes may be formed on opposite surfaces of the plate 12, 112. The upper and lower resistance tubes, or sectors of resistance tube, may then be formed by holding the opposite grooved surfaces of the plate 12, 112 in abutment with planar surfaces of the upper and lower members 8, 108, 10, 110 of the resistance member 6, 106. A device 1, 101 manufactured in this manner functions substantially as described above. However, in the event of damage to the grooves, or if a different groove diameter is required, the plate 12, 112 may simply be exchanged for a new plate 12, 112, without requiring any other component of the device 1, 100 to be changed. An example of such an alternative embodiment of device is illustrated in FIGS. 5 and 6.

Figure 5:
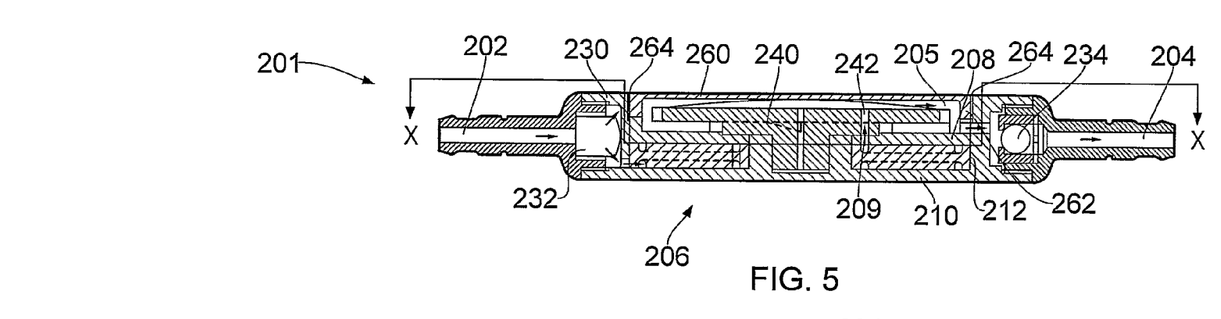
FIG. 5 is a sectional view of another alternative embodiment of device for diverting fluid.
Figure 6:
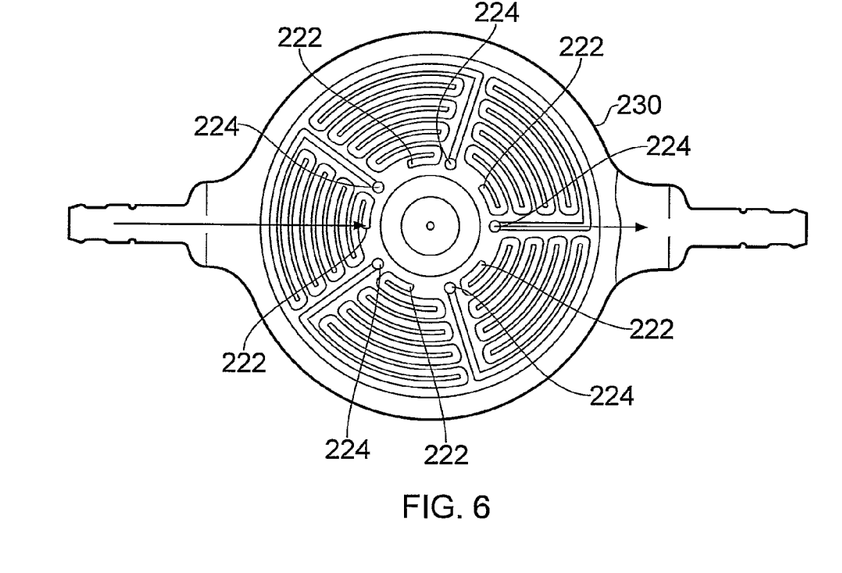
FIG. 6 is a sectional view of the device of FIG. 5, taken along the line XX of FIG. 5.

With reference to FIGS. 5 and 6, the alternative device 201 is substantially similar in construction and operation to the device 101. The device 201 comprises an inlet 202, an outlet 204 and a resistance member 206 operatively coupled between the inlet 202 and the outlet 204. The resistance member comprises an upper member 208, a lower member 210 and a substantially circular plate 212 sandwiched between the upper member 208 and the lower member 210. The lower member 210 forms an integral structure with the inlet 202 and the outlet 204 and with a rim 230 that extends around the circumference of the resistance member 206. The integral structure comprises a casing within which the remaining components of the device 201 are mounted.

The plate 212 has substantially circular upper and lower surfaces. The upper surface of the plate 212 is in contact with a planar surface of the upper member 208 and the lower surface of the plate 212 is in contact with a planar surface of the lower member 210. The upper and lower surfaces of the plate 212 each comprise a plurality of grooves or channels, each of which forms a continuous closed resistance tube when the grooved surface is in contact with a planar surface of a respective upper or lower member 208, 210. Each groove on the upper surface of the plate 212 forms an upper resistance tube that follows a convoluted flow path occupying a single sector of the plane circular area of the upper surface of the plate 212. Similarly, each groove on the lower surface of the plate 212 forms a lower resistance tube that follows a convoluted flow path occupying a corresponding sector of the plane circular area of the lower surface of the plate 212.

As illustrated in FIG. 6, the upper and lower resistance tubes are arranged in a configuration equivalent to that of the upper and lower resistance tubes of the device 101 described above, with corresponding entry and exit points 218, 220, 222 and 224. Fluid flowing through the device 212 therefore follows the same convoluted flow paths as previously described. Each exit point 224 of an upper resistance tube is aligned with a corresponding through passage 209 in the upper member 208.

The device 212 further comprises a selection rotor 240 that is mounted for rotation about the centre point of the resistance tube sectors and comprises a planar face that is held in abutment with, and may be spring loaded against, the surface of the upper member 208 that is opposite to the plate 212. The rotor 240 comprises a single through passage 242, which passage is in fluid communication with the outlet 204 via the chamber 205 within which the rotor 240 is mounted. The opening of the passage 242 on the planar face of the rotor 240 is at the same radial position as the exit points 224 of the upper resistance tubes and corresponding through passages 209 in the upper member 208. The opening of the through passage 242 in the rotor 240 may therefore be brought into communication with the exit point 224 of any one of the upper resistance tubes merely by moving the rotor 240 to the appropriate rotational position. The exit points 224 of the remaining upper resistance tubes are sealed off by the planar face of the rotor 240 sealing off the corresponding through passages in the upper member 208. The remaining functionality of the selection rotor 240 is substantially the same as that of the rotor 140 previously described.

The components of the device 201, including the rotor 240, are held within the casing by a cap 260. The cap 260 is a substantially circular planar element having a circumferential skirt 262. The skirt carries an external thread that engages with a corresponding internal thread on the rim 230 to form a threaded connection 264.

If the resistance tubes defined by the grooves on the plate 212 become occluded or damaged, or if a different diameter of resistance tube is required, it is possible to replace the plate 212 independently of the remainder of the device 201. Once the cap 260 is removed, the rotor 240 and upper member 208 can easily be lifted out of the device to allow the plate 212 to be removed and replaced. The rotor 240 and upper member 208 are then returned to their positions and the device is held together by screwing the cap 260 into place.

A device 212 may be supplied with a series of plates 212, each having grooves of a different diameter or configuration. This enables a medical practitioner to select the most appropriate plate for a particular patient.

It will be understood that while the device 201 illustrated comprises resistance tube sectors and a selection rotor, a device having resistance tube configurations as illustrated in FIG. 2 may also be implemented with a grooved plate 12 contacting planar surfaces of upper and lower members.

To avoid unnecessary duplication of effort and repetition in the text, certain features are described in relation to only one or several aspects or embodiments of the invention. However, it is to be understood that, where it is technically possible, features described in relation to any aspect or embodiment of the invention may also be used with any other aspect or embodiment of the invention.

The invention claimed is:

1. A device for subcutaneous implantation within a human or animal body to divert fluid in a selectively controllable manner from a first part of the human or animal body to a second part thereof, the device comprising:
    an inlet adapted to communicate with a first part of a human or animal body;
    an outlet adapted to communicate with a second part of the human or animal body; and
    a resistance member that communicates with the inlet and the outlet, the resistance member including:
    a first plate including a surface having a groove;
    a second plate that abuts the surface of the first plate and cooperates with the groove to define a resistance flow channel having an entry that communicates with the inlet and at least first and second exits that define different effective lengths of the resistance flow channel from the entry; and
    a rotor supported on one the first plate or the second plate for rotation between at least a first rotational position, wherein communication is provided between the first exit of the resistance flow channel and the outlet, and a second rotational position that position, wherein communication is provided between the second exit of the resistance flow channel and the outlet,
    the rotor being magnetically excitable so that it can be selectively rotated between the first and second rotational positions by a magnet located proximate the device.

2. The device defined in claim 1 wherein the rotor is supported on the first plate for rotation.

3. The device defined in claim 2 further including a structure that resiliently urges the rotor into engagement with the first plate.

4. The device defined in claim 1 wherein the rotor is supported on the second plate for rotation.

5. The device defined in claim 4 further including a structure that resiliently urges the rotor into engagement with the second plate.

6. The device defined in claim 1 wherein the resistance flow channel is a convoluted fluid flow path.

7. The device defined in claim 1 wherein the resistance flow channel includes first and second sectors, the first exit of the resistance flow channel being provided in the first sector and the second exit of the resistance flow channel being provided in the second sector.

8. The device defined in claim 7 wherein each of the first and second sectors of the resistance flow channel is a convoluted fluid flow path.

9. The device defined in claim 1 further including a ratchet or brake that releasably retains the rotor in a selected rotational orientation relative to the one of the first plate or the second plate on which the rotor is supported for rotation.

10. The device defined in claim 1 further including a marker that is provided on the rotor.

11. The device defined in claim 10 wherein the marker is a magnetic marker.

12. The device defined in claim 1 further including a filter provided at the inlet.

13. The device defined in claim 1 further including an anti-reflux mechanism provided at the outlet.

14. A device for subcutaneous implantation within a human or animal body to divert fluid in a selectively controllable manner from a first part of the human or animal body to a second part thereof, the device comprising:
    an inlet adapted to communicate with a first part of a human or animal body;
    an outlet adapted to communicate with a second part of the human or animal body; and
    a resistance member that communicates with the inlet and the outlet, the resistance member including:
    a first plate including a surface having a first groove;
    a second plate including a surface having a second groove;
    a third plate including a first surface and a second surface, wherein
        the first surface of the third plate abuts the surface of the first plate and cooperates with the first groove to define a first resistance flow channel having an entry that communicates with the inlet and at least first and second exits that define different effective lengths of the first resistance flow channel from the entry, and
        the second surface of the third plate abuts the surface of the second plate and cooperates with the second groove to define a second resistance flow channel having at least first and second entries that respectively communicate with the at least first and second exits of the first resistance flow channel and at least first and second exits that define different effective lengths of the second resistance flow channel from the entry; and
    a rotor supported on one of the first plate or the second plate for rotation between at least a first rotational position, wherein communication is provided between the first exit of the resistance flow channel and the outlet, and a second rotational position that position, wherein communication is provided between the second exit of the resistance flow channel and the outlet, the rotor being magnetically excitable so that it can be selectively rotated between the first and second rotational positions by a magnet located proximate the device.

15. The device defined in claim 14 wherein the rotor is supported on the first plate for rotation.

16. The device defined in claim 15 further including a structure that resiliently urges the rotor into engagement with the first plate.

17. The device defined in claim 14 wherein each of the first and second resistance flow channels is a convoluted fluid flow path.

18. The device defined in claim 14 further including a ratchet or brake that releasably retains the rotor in a selected rotational orientation relative to the one of the first plate or the second plate on which the rotor is supported for rotation.

19. The device defined in claim 14 further including a marker that is provided on the rotor.

20. The device defined in claim 14 further including a filter provided at the inlet and an anti-reflux mechanism provided at the outlet.

* * * * *